US009663565B2

(12) United States Patent
Jung et al.

(10) Patent No.: US 9,663,565 B2
(45) Date of Patent: May 30, 2017

(54) INSULINOTROPIC PEPTIDE DERIVATIVE WITH MODIFIED N-TERMINAL CHARGE

(71) Applicant: HANMI PHARM. CO., LTD., Hwaseong-si, Gyeonggi-do (KR)

(72) Inventors: Sung Youb Jung, Suwon-si (KR); Sang Youn Hwang, Hwaseong-si (KR); In Young Choi, Yongin-si (KR); Sung Hee Park, Seongnam-si (KR); Se Chang Kwon, Seoul (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 14/758,842

(22) PCT Filed: Jan. 3, 2014

(86) PCT No.: PCT/KR2014/000025
§ 371 (c)(1),
(2) Date: Jul. 1, 2015

(87) PCT Pub. No.: WO2014/107035
PCT Pub. Date: Jul. 10, 2014

(65) Prior Publication Data
US 2015/0329611 A1 Nov. 19, 2015

(30) Foreign Application Priority Data

Jan. 3, 2013 (KR) .................. 10-2013-0000766
Jan. 2, 2014 (KR) .................. 10-2014-0000031

(51) Int. Cl.
C07K 14/605 (2006.01)
C07K 14/575 (2006.01)
C07K 14/62 (2006.01)
A61K 38/22 (2006.01)
A61P 7/12 (2006.01)

(52) U.S. Cl.
CPC .......... C07K 14/605 (2013.01); C07K 14/575 (2013.01); C07K 14/62 (2013.01)

(58) Field of Classification Search
CPC ..... C07K 14/605; C07K 14/62; C07K 14/575
See application file for complete search history.

(56) References Cited

U.S. PATENT DOCUMENTS

| 5,164,366 | A | 11/1992 | Balschmidt et al. |
| 5,837,218 | A * | 11/1998 | Peers .................. A61K 51/088 424/1.65 |
| 2008/0119390 | A1 | 5/2008 | Mozes |
| 2010/0105877 | A1 | 4/2010 | Song et al. |
| 2010/0204451 | A1 * | 8/2010 | Jung .................. C07K 14/46 530/350 |
| 2010/0330108 | A1 * | 12/2010 | Song ................ A61K 47/48415 424/179.1 |

FOREIGN PATENT DOCUMENTS

| KR | 10-1991-0700262 A | 3/1991 | |
| KR | 10-2008-0064750 A | 7/2008 | |
| KR | WO 2010/107256 A2 * | 9/2010 | ....... A61K 47/48215 |
| WO | 97/46584 A1 | 12/1997 | |
| WO | 99/07404 A1 | 2/1999 | |
| WO | 01/04156 A1 | 1/2001 | |
| WO | 2009011544 A2 | 1/2009 | |
| WO | 2009069983 A2 | 6/2009 | |
| WO | 2012165915 A2 | 12/2012 | |

OTHER PUBLICATIONS

Sequence listing for WO 2010/107256 A2, pp. 1-2, accessed Jun. 8, 2016.*
Wang et al, Des-Met Carboxyl-terminally Modified Analogues of Bombesin Function as Potent Bombesin Receptor Antagonists, Partial Agonists, or Agonists, The Journal of Biological Chemistry, 1990, 265, pp. 15695-15703.*
Schneider et al, The Design of Efficient alpha-Helical C-Capping Auxiliaries, J. Am. Chem. Soc., 1998, 120, pp. 2764-2767.*
Irena Fonda et al., "Improvement of potential therapeutic value of tumor necrosis-α (TNF-α) by charge modulation in the tip region," Eur. Cytokine Netw., Mar. 1, 2005, pp. 17-26, vol. 16, No. 1.
Anna On-Yee Chan et al., "Modifications of N-Terminal α-Amino Groups of Peptides and Proteins Using Ketenes," Journal of the American Chemical Society, 2012, pp. 2589-2598, vol. 134.
Erhard G. Siegel et al., "Biological activity of GLP-1-analogues with N-terminal modifications," Regulatory Peptides, 1999, pp. 93-102, vol. 79.
Baptist Gallwitz et al., "GLP-1-analogues resistant to degradation by dipeptidyl-peptidase IV in vitro," Regulatory Peptides, 2000, pp. 103-111, vol. 86.
International Searching Authority, International Search Report of PCT/KR2014/000025 dated Apr. 22, 2014.
European Patent Office; Communication dated Apr. 29, 2016 in counterpart European Application No. 14735289.2.

(Continued)

Primary Examiner — Julie Ha
Assistant Examiner — Li Ni Komatsu
(74) Attorney, Agent, or Firm — Sughrue Mion, PLLC

(57) ABSTRACT

The present invention relates to an insulinotropic peptide derivative with a modified N-terminal charge and a pharmaceutical composition including the same. Specifically, the insulinotropic peptide derivative is characterized in that the N-terminal positive charge of the insulinotropic peptide is modified to a neutral or net negative charge at neutral pH. The insulinotropic peptide derivative according to the present invention is rapidly dissociated from the GLP-1 receptor owing to the above modification in the N-terminal charge, and exhibits enhanced insulinotropic ability and blood glucose-lowering activity compared to the native insulinotropic peptide while maintaining its stability in blood. Accordingly, the insulinotropic peptide derivative of the present invention is very useful for the treatment of type 2 diabetes.

13 Claims, 4 Drawing Sheets

(56) References Cited

OTHER PUBLICATIONS

Son, Sohee et al: "Preparation and Structural, Biochemical, and Pharmaceutical Characterizations of Bile Acid-Modified Long-Acting Exendin-4 Derivatives", Journal of Medicinal Chemistry, American Chemical Society. US. vol. 52. No. 21. 2009, pp. 6889-6896, XP008157488,ISSN: 0022-2623, DOI: 10.1021 /JM901153X.

Jin, C H et al: "A new orally available glucagon-like peptide-1 receptor agonist, biotinylated exendin-4, displays improved hypoglycemic effects in db/db mice". Journal of Controlled Release. Elsevier, vol. 133, No. 3, 2009, pp. 172-177, XP025893044,ISSN: 0168-3659, DOI: 10.1016/ J.JCONREL.2008.09.091.

Chae, S Y et al: "The fatty acid conjugated exendin-4 analogs for type 2 antidiabetic therapeutics", Journal of Controlled Release, Elsevier, vol. 144, No. 1, 2010, pp. 10-16, XP027036550,ISSN: 0168-3659.

\* cited by examiner

\* : p < 0.05

INSULINOTROPIC PEPTIDE DERIVATIVE WITH MODIFIED N-TERMINAL CHARGE

CROSS REFERENCE TO RELATED APPLICATIONS

This is a National Stage of International Application No. PCT/KR2014/000025 filed Jan. 3, 2014, claiming priority based on Korean Patent Application No. 10-2013-0000766 filed Jan. 3, 2013 and Korean Patent Application No. 10-2014-0000031 filed Jan. 2, 2014, the contents of all of which are incorporated herein by reference in their entirety.

TECHNICAL FIELD

The present invention relates to an insulinotropic peptide derivative which is modified to have increased insulinotropic activity and blood glucose level-lowering activity, and a pharmaceutical composition containing the same. The insulinotropic peptide derivative according to the present invention is characterized in that the N-terminal charge of the insulinotropic peptide is modified to a neutral or net negative charge.

BACKGROUND ART

Peptides can be easily denatured due to their low stability, lose their activities via degradation by in-vivo proteolytic enzymes, and are so small so as to be easily removed through the kidney. Accordingly, in order to maintain the blood levels and the titers of a pharmaceutical drug containing a peptide as a pharmaceutically active component, it is necessary to frequently administer the peptide drug to a patient.

However, most peptide drugs are administered as injection preparations and frequent administration is necessary for the maintenance of the blood level of the physiologically active peptides, thus causing a severe pain for the patients. To solve these problems, many efforts have been made to increase the stability of peptide drugs in blood and to maintain the drugs in the blood at high level for a prolonged period of time, thereby maximizing the pharmaceutical efficacy of the drugs.

In particular, the long-acting preparations of such peptide drugs therefore need to increase their stability while simultaneously maintaining their titers at sufficiently high levels without causing any immune responses in patients. In this regard, as methods for stabilizing the peptides, and inhibiting the degradation by a proteolytic enzyme, attempts have been made to modify specific amino acid sequences which are sensitive to proteolytic enzymes.

For example, GLP-1 (7-37 or 7-36 amide), which has a therapeutic effect of lowering the blood glucose level for treating type 2 diabetes, has a short physiological half-life of about 4 minutes or less, due to loss of the titers of GLP-1 through the cleavage between the 8th amino acid (Ala) and the 9th amino acid (Asp) by a dipeptidyl peptidase IV (DPP IV). In this regard, GLP-1 derivatives, in which $Ala^8$ is substituted with Gly, Leu, or D-Ala to increase the resistance to DPP IV while maintaining the physiological activity, have been developed. Moreover, the N-terminal amino acid of GLP-1, $His^7$, is critical for the GLP-1 activity, and serves as a target for DPP IV. Accordingly, the N-terminus is modified to an alkyl or acyl group, and $His^7$ is subjected to N-methylation or alpha-methylation, to increase its resistance to DPP IV, and to maintain its physiological activity. Although it was confirmed that the stability was improved due to an increase in their resistance to DPP IV there was also a report that the receptor affinity of the derivatives obtained by modifying $His^7$ was considerably reduced and the secretory capacity of cAMP was reduced at the same concentration (see, Galiwitz al., Regulatory Peptide 79: 9-102, 1999; Galiwitz et. al., Regulatory Peptide 86: 103-111, 2000).

In addition, among the insulinotropic peptides such as GLP-1, exendin-4 is composed of a sequence of His-Gly instead of His-Ala, which is a sequence of GLP-1 acting as a substrate for DDP IV. Accordingly, exendin-4 has resistance to DPP IV and higher physiological activity than that of GLP-1. Thus, exendin-4 has a longer in-vivo half-life than that of GLP-1. However, although the in-vivo half-life of exendin-4 is longer than that of GLP-1, commercially available exendin-4 (exenatide) must be administered to a patient twice a day via injection, and this is a major inconvenience for patients.

Under these circumstances, the present inventors have made various efforts to increase the activities and stability in blood of insulinotropic peptides and discovered that insulinotropic peptide derivatives with a modified N-terminal charge can exhibit superior pharmacokinetics and higher insulinotropic activities compared to those of a native insulinotropic peptide, thereby completing the present invention.

DISCLOSURE

Technical Problem

An objective of the present invention is to provide an insulinotropic peptide derivative having increased insulinotropic activities and hence excellent blood glucose level-lowering activities.

Another objective of the present invention is to provide a pharmaceutical composition for the treatment of diabetes containing the above insulinotropic peptide derivative as an active ingredient.

A further objective of the present invention is to provide a method for treating diabetes using the above insulinotropic peptide derivative.

Technical Solution

In an aspect for accomplishing the above objectives, the present invention provides an insulinotropic peptide derivative in which the N-terminal charge of a native insulinotropic peptide is modified.

In an embodiment, the present invention provides an insulinotropic peptide derivative in which the N-terminal amino group or N-terminal amino acid residue of the insulinotropic peptide is modified to have a neutral or net negative charge.

In another embodiment, the insulinotropic peptide derivative according to the present invention is characterized in that it is a chemically modified derivative in which the alpha-amino group of the N-terminal histidine residue of the insulinotropic peptide is removed or substituted, or the alpha-carbon is removed, thereby having a neutral or net negative charge.

In still another embodiment, the insulinotropic peptide derivative according to the present invention is characterized in that the derivative is introduced with a chemical modification corresponding to at least one selected from the group consisting of: removing the N-terminal amino group of the insulinotropic peptide; substituting the N-terminal amino group with a hydroxyl group; modifying the N-terminal amino group with two methyl groups; substituting the N-terminal amino group with a carboxyl group; removing the alpha-carbon of the N-terminal histidine residue thereby leaving only the imidazoacetyl group; and removing the N-terminal amino group while substituting the C-terminal carboxyl group with 3-amino propylamide.

In still another embodiment, the insulinotropic peptide derivative according to the present invention is characterized in that the N-terminal histidine residue of insulinotropic peptide is substituted with a material selected from the group consisting of desamino-histidyl, dimethyl-histidyl, beta-hydroxy imidazopropionyl, 4-imidazoacetyl, and beta-carboxyimidazopropionyl.

In still another embodiment, the insulinotropic peptide derivative according to the present invention is characterized in that the N-terminal histidine residue of the insulinotropic peptide is substituted with desamino-histidyl, and the C-terminal carboxyl group is substituted with 3-amino propylamide.

In still another embodiment, the insulinotropic peptide derivative according to the present invention is characterized in that the insulinotropic peptide has binding activity with a GLP-receptor.

In still another embodiment, the insulinotropic peptide derivative according to the present invention is characterized in that the insulinotropic peptide is GLP-1 represented. SEQ ID NO: 1, exendin-4 represented by SEQ ID NO: 2, exendin-3 represented by SEQ ID NO: 3, oxyntomodulin represented by SEQ ID NO: 5, GIP represented by SEQ ID NO: 6, or an analogue thereof.

In still another embodiment, the insulinotropic peptide derivative according to the present invention is characterized in that it has a higher dissociation constant (Kd) from a GLP-1 receptor due to the modification in the N-terminal charge than that of a native insulinotropic peptide.

In still another embodiment, the insulinotropic peptide derivative of the present invention is characterized in that the N-terminal histidine residue of GLP-1, exendin-4, exendin-3, oxyntomodulin, GIP, or an analogue thereof is substituted with desamino-histidyl, dimethyl-histidyl, beta-hydroxy imidazopropionyl, 4-imidazoacetyl, or beta-carboxyimidazopropionyl.

In still another embodiment, the insulinotropic peptide derivative of the present invention is characterized in that the N-terminal histidine residue of GLP-1, exendin-4, exendin-3, oxyntomodulin, GIP, or an analogue thereof is substituted with desamino-histidyl, and the C-terminal carboxyl group of GLP-1, exendin-4, exendin-3, oxyntomodulin, GIP, or an analogue thereof is substituted with 3-amino propylamide.

In still another embodiment, the insulinotropic peptide derivative of the present invention is characterized in that it is selected from the group consisting of: desamino-histidyl-exendin-4 prepared by removing the N-terminal amino group of exendin-4; beta-hydroxy imidazopropionyl-exendin-4 prepared by substituting the N-terminal amino group of exendin-4 with a hydroxyl group; beta-carboxyimidazopropionyl-exendin-4 prepared by substituting the N-terminal amino group of exendin-4 with a carboxyl group; dimethyl-histidyl-exendin-4 prepared by modifying the N-terminal amino group of exendin-4 with two methyl groups; and imidazoacetyl-exendin-4 prepared by removing the alpha-carbon of histidine, which is the first amino acid of exendin-4.

In still another embodiment, the insulinotropic peptide derivative of the present invention is characterized in that it is DA-exendin-4-propyl-amide prepared by removing the N-terminal amino group of exendin-4 while substituting the C-terminal carboxyl group thereof with 3-amino propylamide.

In another aspect, the present invention provides a pharmaceutical composition for the treatment of diabetes containing as an active ingredient the insulinotropic peptide derivative in which the N-terminal charge of the insulinotropic peptide is modified as described above.

In still another embodiment, the present invention provides a method for treating diabetes including administering a therapeutically effective amount of the insulinotropic peptide derivative, in which the N-terminal charge is modified as described above, to a subject in need thereof.

Advantageous Effects

The insulinotropic peptide derivative with a modified N-terminal charge in accordance with the present invention can be rapidly dissociated from the GLP-1 receptor due to the modification in the N-terminal charge, so as to prevent clearance of the insulinotropic peptide and reduce desensitization. Also, the insulinotropic peptide derivative with a modified N-terminal charge according to the present invention can exhibit improvements of insulinotropic activity and in-vivo blood glucose level-lowering activity due to a change in the binding activity with the GLP-1 receptor compared to those of a native insulinotropic peptide. Therefore, the insulinotropic peptide derivative according to the present invention can be very effectively used for the treatment of diabetes.

DESCRIPTION OF DRAWINGS

FIGS. 1a through 1e show coupling curves according to concentrations of the insulinotropic peptide derivative with a modified N-terminal charge according to the present invention with GLP-1 receptors, wherein FIG. 1a represents native exendin-4, FIG. 1b CA-exendin-4, FIG. 1c DA-exendin-4, FIG. 1d DA-exendin-4-propyl-amide, and FIG. 1e HY-exendin-4.

BEST MODE

Figure 1A:
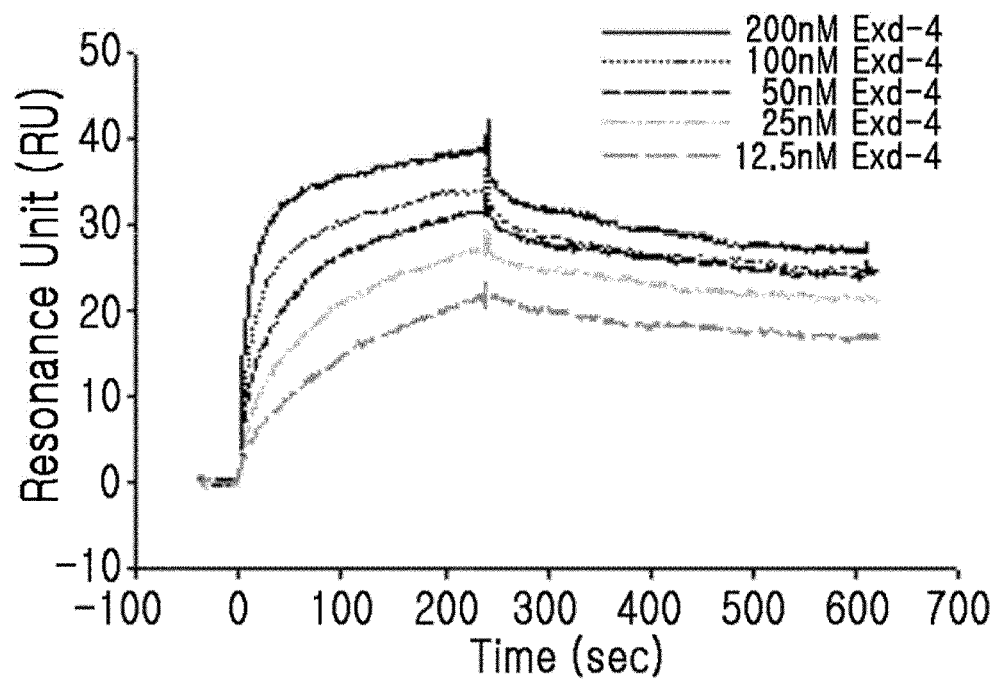
Figure 1B:
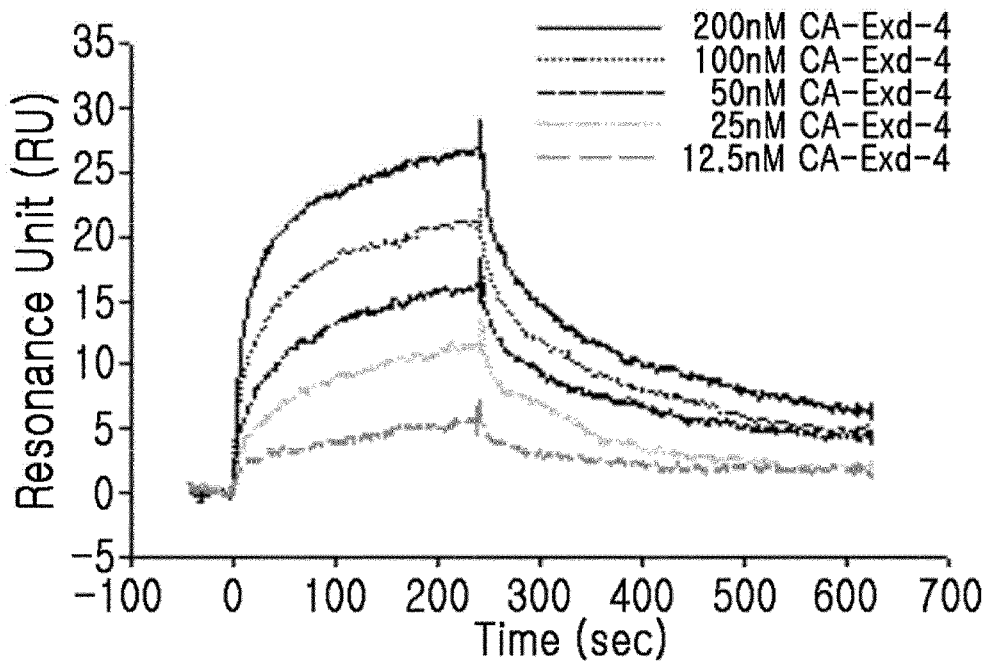
Figure 1C:
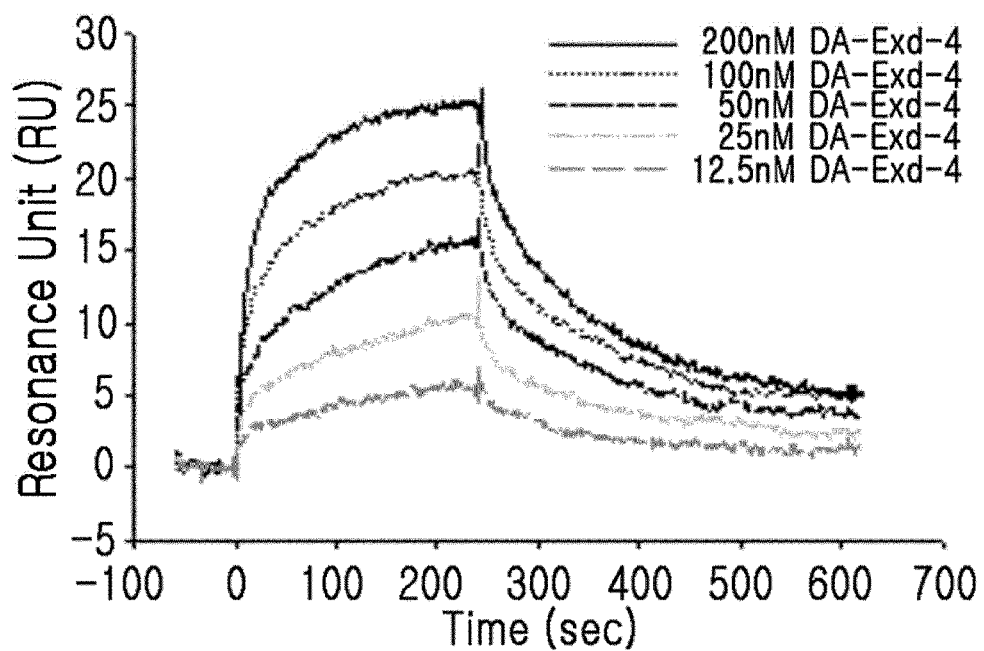
Figure 1D:
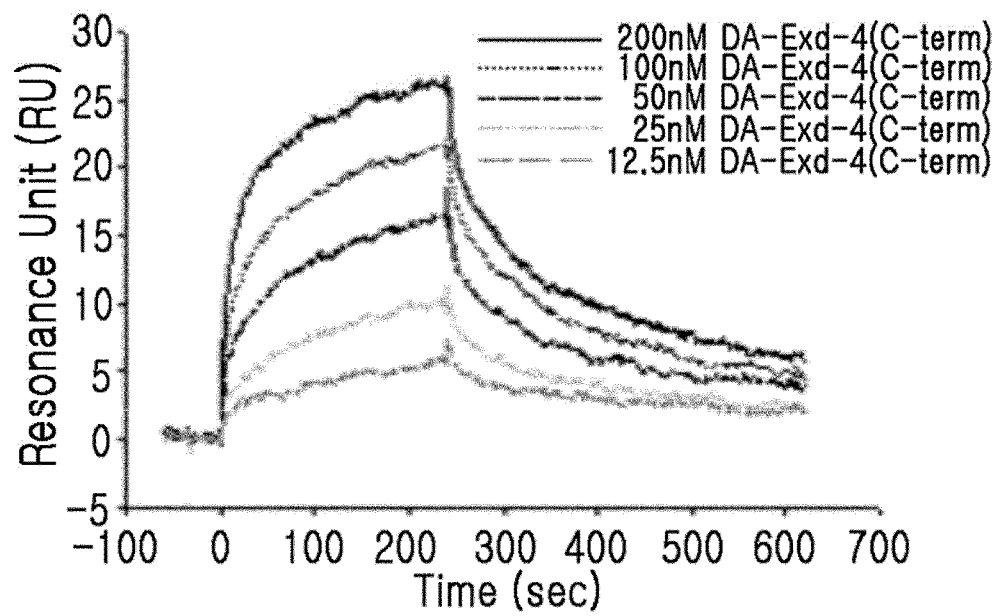
Figure 1E:
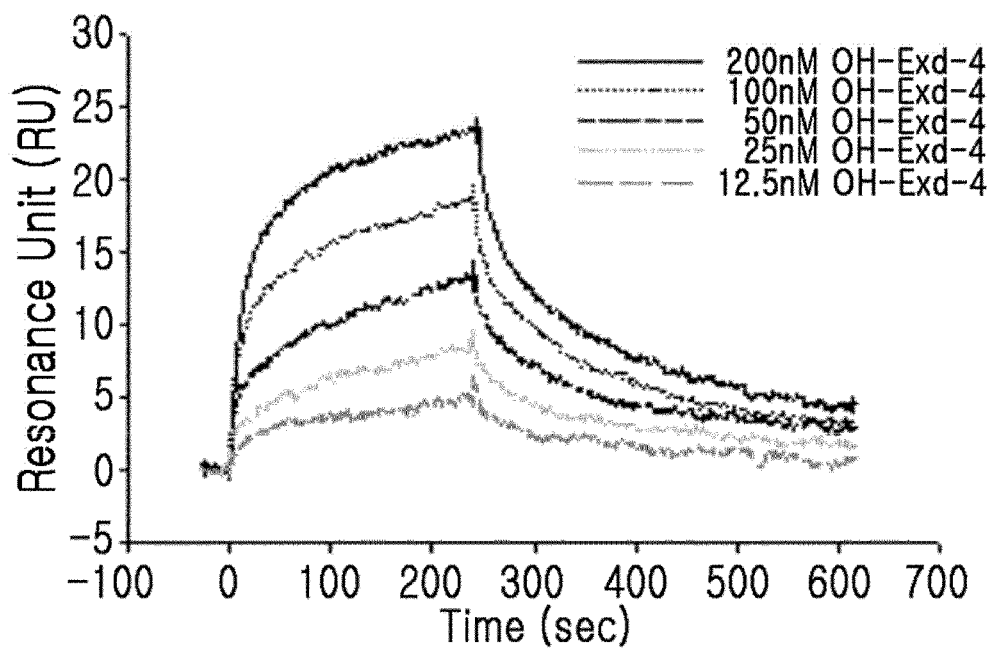

The present invention provides an insulinotropic peptide derivative having a modification on its N-terminal charge.

The insulinotropic peptide derivative according to the present invention is characterized by the modification of the N-terminal charge of the insulinotropic peptide thereby rapidly dissociating it from the receptor.

The term "insulinotropic peptide derivative" as used herein refers to a derivative in which the N-terminal positive charge of a native insulinotropic peptide, its analogue or a fragment thereof is modified to a neutral or net negative charge by a chemical, genetic, or physical manipulation while retaining its unique insulinotropic function.

Specifically, the insulinotropic peptide derivative according to the present invention is preferably a derivative in which the N-terminal amino group or N-terminal amino acid residue of the insulinotropic peptide is chemically modified to have a neutral or net negative charge, and more preferably, a derivative in which the positive charge on the first amino acid residue of the N-terminal of the insulinotropic peptide is modified to a neutral or net negative charge.

The term "insulinotropic peptide" as used herein refers to a peptide having insulinotropic function for stimulating the synthesis and expression of insulin in a pancreatic beta cell. Any insulinotropic peptide suitable for the present invention may be used, without limitation, as long as it shows physiological activity by binding with a GLP-1 receptor. Non-limiting examples thereof include GLP-1 (7-37) of SEQ ID NO: 1, exendin-4 of SEQ ID NO: 2, exendin-3 of SEQ ID NO: 3, oxynthomodulin of SEQ ID NO: 5, a glucose-dependent insulinotropic polypeptide of SEQ ID NO: 6, and an analogue or fragment thereof.

The term. "insulinotropic peptide analogue" as used herein refers to a peptide in which at least one amino acid of an amino acid sequence of a native insulinotropic peptide is modified, and which has an insulinotropic function. Preferably, the analogue of the insulinotropic peptide of the present invention refers to a polypeptide showing at least 80% amino acid sequence homology to that of the native insulinotropic peptide, and it may be in a form wherein the amino acid residues are partly chemically substituted (e.g., alpha-methylation, alpha-hydroxylation), removed (e.g., deamination), or modified (e.g., N-methylation).

In a preferred embodiment of the invention, the insulinotropic peptide analogue refers to showing equivalent or higher insulinotropic activity compared to that of the native insulinotropic peptide, but range of the insulinotropic peptide analogues of the present invention is not necessarily limited to those having the insulinotropic activity at this level.

The term "fragment of an insulinotropic peptide" according to the present invention refers to a fragment having at least one amino acid added or removed at the N-terminus or the C-terminus of the native insulinotropic peptide while retaining the insulinotropic function. The added amino acid may be a non-naturally occurring amino acid (e.g., D-type amino acid).

GLP-1 is a hormone secreted by the small intestine, and usually promotes biosynthesis and secretion of insulin, inhibits glucagon secretion, and promotes glucose uptake by the cells. In the small intestine, a glucagon precursor is decomposed into three peptides, i.e., glucagon, GLP-1, and GLP-2. Here, the GLP-1 refers to GLP-1 (1-37), which is in the form without an insulinotropic function, and is processed to become an active form of GLP-1 (7-37). The GLP-1 (7-37) has an amino acid sequence represented by SEQ ID NO: 1.

Preferably, a GLP-1 analogue may be selected from the group consisting of Arg$^{34}$-GLP-1(7-37), Gly$^8$-GLP-1(7-36)-amide, Gly$^8$-GLP-1(7-37), Val$^8$-GLP-1(7-36)-amide, Val$^8$-GLP-1(7-37), Val$^8$Asp$^{22}$-GLP-1 (7-36)-amide, Val$^8$Asp$^{22}$-GLP-1(7-37), Val$^8$Glu$^{22}$-GLP-1(7-36)-amide, Val$^8$Glu$^{22}$-GLP-1(7-37), Val$^8$Lys$^{22}$-GLP-1(7-36)-amide, Val$^8$Lys$^{22}$-GLP-1(7-37), Val$^8$Arg$^{22}$-GLP-1 (7-36)-amide, Val$^8$Arg$^{22}$-GLP-1 (7-37), Val$^8$His$^{22}$-GLP-1(7-36)-amide, Val$^8$His$^{22}$-GLP-1(7-37), Val$^8$Trp$^{16}$Glu$^{22}$-GLP-1(7-37), Val$^8$Glu$^{22}$Val$^{25}$-GLP-1(7-37), Val$^8$Tyr$^{16}$Glu$^{22}$-GLP-1(7-37), Val$^8$Trp$^{16}$Glu$^{22}$-GLP-1(7-37), Val$^8$Leu$^{16}$Glu$^{22}$-GLP-1(7-37), Val$^8$Tyr$^{18}$Glu$^{22}$-GLP-1(7-37), Val$^8$Glu$^{22}$His$^{38}$-GLP-1 (7-37), Val$^8$Glu$^{22}$Ile$^{33}$-GLP-1(7-37), Val$^8$Trp$^{16}$Glu$^{22}$Val$^{28}$Ile$^{33}$-GLP-1(7-37), Val$^8$Trp$^{16}$Glu$^{22}$Ile$^{33}$-GLP-1(7-37), Val$^8$Glu$^{22}$Val$^{28}$Ile$^{33}$-GLP-1(7-37), and Val$^8$Trp$^{16}$Glu$^{22}$Val$^{28}$-GLP-1(7-37), but is not limited thereto.

As another type of insulinotropic peptide, exendin-4 is a polypeptide consisting of 39 amino acids that shows 53% amino acid sequence similarity with GLP-1 and has an amino acid sequence represented by SEQ ID NO: 2. Exendin-3 has an amino acid sequence represented SEQ ID NO: 3 and it is an exendin-4 analogue wherein only amino acids at positions 2 and 3 differ from exendin-4. Exendin-3 is one in which amino acids at positions 2 and 3 of exendin-4 are substituted with serine and aspartic acid, respectively, and it can be represented by Ser$^2$Asp$^3$-exendin-4(1-39). As another exendin-4 analogue, ZP-10, in which amino acids at positions 38 and of exendin-4 are substituted with serine and lysine, respectively, represented as Ser$^{38}$Lys$^{39}$-exendin-4 (1-39)-LysLysLysLysLys-amide and has an amino acid sequence of SEQ ID NO: 4.

Oxyntomodulin refers to a peptide produced from a pre-glucagon, which is a precursor of glucagon, and is released from L-cells of the small intestine in proportion to the nutrient uptake along with GLP-1. Oxyntomodulin is a peptide hormone consisting of 37 amino acids represented by SEQ ID NO: 5, and shows the effects of food intake inhibition, satiety enhancement, and lypolysis of glucagon.

The glucose-dependent insulinotropic peptide (GIP) is an incretin that regulates insulin secretion in the pancreas in a glucose-dependent manner in response to intestinal absorption of nutrients. The GIP consists of 42 amino acids described in SEQ ID NO: 6 and is secreted from the cell K of the small intestine. GIP not only stimulates insulin secretion in a glucose-dependent manner but also promotes insulin synthesis, induces proliferation of and inhibits apoptosis.

The methods used for manufacturing a native insulinotropic peptide, its analogue, or a fragment thereof as described above may be used independently or in combinations thereof. For example, an insulinotropic peptide, which differs in at least one amino acid residue of an amino acid sequence from that of the native insulin and has deamination at the N-terminal amino acid residue, is included in the present invention.

In a specific embodiment, the native insulinotropic peptide and the modified insulinotropic peptide derivative used in the present invention may be synthesized by a solid phase synthesis protocol, and most native polypeptides including the native insulinotropic peptide may also be produced by recombinant methods.

The GLP-1, exendin-4, exendin-3, oxyntomodulin, or GIP analogue may refer to a peptide, in which at least one amino acid of the native GLP-1, exendin-4, or exendin-3 is substituted, removed, and/or added; or at least one amino acid residue is chemically modified, e.g., by alkylation, acylation, esterification, or amidation, and has the native insulinotropic activity.

Concerning GLP-1 and exendin 3 or exendin-4 analogues, International Publication. WO97/046584 discloses exendin analogues, in which the C-terminal end of GLP-1 or exendin-4 is partially removed or substituted with a non-natural amino acid, i.e., norleucine; and International. Publication WO99/07404 discloses exdendin agonist compounds with substitution of amino acids of exendin including non-natural amino acids, such as pentylglycine, homoproline, and tert-butylglycine; and US Patent Application Publication No. 2008/0119390 discloses exendin agonist compounds in which exdendin-4 is configured to have a shorter amino acid sequence than the native type or substituted with other amino acids, the entire contents of which are incorporated herein by reference.

The insulinotropic peptide derivative according to the present invention is characterized in that the N-terminal amino group or N-terminal amino acid residue of the native insulinotropic peptide, its analogue, or a fragment thereof is modified to have a neutral or net negative charge as described above.

Preferably, the insulinotropic peptide derivative according to the present invention is characterized in that the positive charge on the first amino acid residue of the N-terminal of the insulinotropic peptide is chemically modified to a neutral or net negative charge.

The insulinotropic peptide derivative in which the N-terminal positive charge of the insulinotropic peptide is chemically modified to a neutral or net negative charge according to the present invention is characterized in that it has a higher dissociation constant (Kd) from the GLP-1 receptor compared to that of the native insulinotropic peptide. The insulinotropic peptide derivative according to the present invention is modified to have preferably a more than two-fold, more preferably a more than three-fold and most preferably a more than six-fold higher dissociation constant from the GLP-1 receptor compared to that of the native insulinotropic peptide, but is not limited thereto.

The insulinotropic peptide derivative, in which the N-terminal positive charge of the insulinotropic peptide is modified to a neutral or net negative charge according to the present invention, may be produced by various methods known in the art. This insulinotropic peptide derivative may be modified to have a neutral or net negative charge by the removal or substitution of alpha-amino-terminal histidine residues, or removal of alpha-carbon.

More preferably, the insulinotropic peptide derivative with a modified N-terminal charge according to the present invention may include a derivative prepared by removing the amino group of the N-terminal histidine of the insulinotropic peptide (desamino-histidyl derivative), a derivative prepared by substitution of the N-terminal amino group with a hydroxyl group (beta-hydroxyimidazopropionyl derivative), a derivative prepared by modification of the N-terminal amino group with two methyl groups (dimethyl-histidyl derivative), a derivative prepared by substitution of the N-terminal amino group with a carboxyl group (beta-carboxyimidazopropionyl derivative), or a derivative prepared by removal of the alpha-carbon of a N-terminal histidine residue to leave only the imidazoacetyl group (imidazoacetyl derivative). Any kind of the insulinotropic peptide derivative with a modified N-terminal amino group may be within the scope of the present invention as long as its N-terminal positive charge can be modified to a neutral or net negative charge.

The insulinotropic peptide derivative with a modified N-terminal charge as described above may be represented by the following structures:

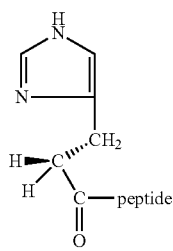

desamino-histidyl (DA)
insulinotropic peptide

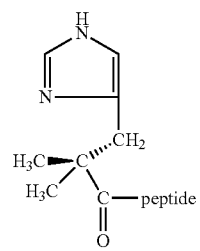

dimethyl-histidyl (DM)
insulinotropic peptide

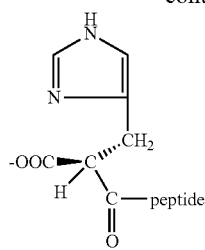

beta-carboxy imidazopropionyl (CX)
insulinotropic peptide

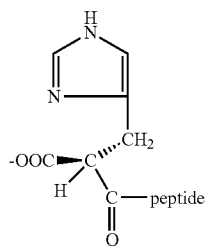

beta-carboxy imidazopropionyl (CX)
insulinotropic peptide

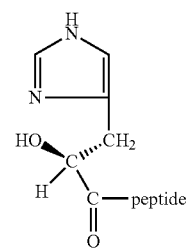

beta-hydroxy imidazopropionyl (HY)
insulinotropic peptide

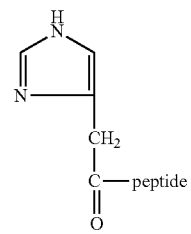

4-imidazoacetyl (CA)
insulinotropic peptide

Furthermore, the insulinotropic peptide derivative with a modified N-terminal charge according to the present invention may include a derivative in which the C-terminal carboxyl group of the desamino-histidyl derivative with removal of the N-terminal amino group is substituted with propylaminde as described above.

The insulinotropic peptide derivative with a modified N-terminal charge as described above can be represented by the following structure:

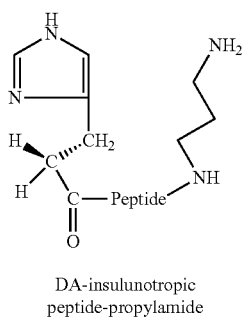

DA-insulunotropic
peptide-propylamide

Still more preferably, the insulinotropic peptide derivative according to the present invention may be a derivative in which the N-terminal histidine residue of GPL-1, exendin-4, exendin-3, oxyntomodulin, GIP, its analogue or a fragment thereof is substituted with desamino-histidyl, dimethyl-histidyl, beta-hydroxy imidazopropionyl, 4-imidazoacetyl, or beta-carboxy imidazopropionyl, thereby modifying its N-terminal charge.

In an aspect, the insulinotropic peptide derivative with a modified N-terminal charge according to the present invention may be represented by the following Formula 1:

R1-X—R2  <Formula 1> wherein R1 is selected from the group consisting of desamino-histidyl, dimethyl-histidyl, beta-hydroxy imidazopropionyl, 4-imidazoacetyl, and beta-carboxy imidazopropionyl;

R2 is —NH$_2$ or —OH,

X is Ala-Glu-Gly-Thr-Phe-Thr-Ser-Asp-Val-Ser-Ser-Tyr-Leu-Glu-Gly-Gln-Ala-Ala-Lys-Glu-Phe-Ile-Ala-Trp-Leu-Val-Lys-Gly-Arg-Gly (SEQ ID NO: 7);

Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (SEQ ID NO: 8);

Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser (SEQ ID NO: 9); or

Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala (SEQ ID NO: 10).

In a preferred embodiment of the present invention, the insulinotropic peptide derivative is a derivative with modification of the N-terminal charge of exendin-4, and it may be selected from the group consisting of desamino-histidyl-exendin-4 (DA-exendin-4) prepared by removing the N-terminal amino group of exendin-4; beta-hydroxy imidazopropionyl-exendin-4 (HY-exendin-4) prepared by substituting the N-terminal amino group of exendin-4 with a hydroxyl group; beta-carboxyimidazopropionyl-exendin-4 (CX-exendin-4) prepared by substituting the N-terminal amino group of exendin-4 with a carboxyl group; dimethyl-histidyl-exendin-4 (DM-exendin-4) prepared by modifying the N-terminal amino group of exendin-4 with two methyl residues; and imidazoacetyl-exendin-4 (CA-exendin-4) prepared by removing the alpha-carbon of histidine, which is the first amino acid of exendin-4.

Further, the insulinotropic peptide derivative of the present invention may be one in which the N-terminal histidine residue of GLP-1, exendin-4, exendin-3, oxyntomodulin, GIP, its analogue, or a fragment thereof is substituted with desamino-histidyl, and the C-terminal carboxyl group thereof is substituted with 3-amino propylamide.

In another aspect, the insulinotropic peptide derivative with a modified N-terminal charge may include DA-exendin-4-propyl-amide prepared by removing the N-terminal amino group of exendin-4 while substituting the C-terminal carboxyl group of desamino-histidyl-exendin-4 (DA-exendin-4) with 3-amino propylamide.

The above derivatives are those in which the alpha-amino group of the amino-terminal histidine residue is removed or substituted or the alpha-carbon is removed. The amino acid sequences are not particularly limited as long as physiological activities of the derivatives are maintained.

Like the exendin-4 derivative, substitution or removal may be applied even to the N-terminal end of other types of insulinotropic peptides, e.g., exendin-3, GLP-1, oxyntomodulin, and GIP. This may be applied even to their analogues and fragments thereof as long as their insulinotropic activities are maintained.

The insulinotropic peptide derivative with a modified N-terminal charge according to the present invention can be rapidly dissociated from the GLP-1 receptor, thus preventing clearance of the insulinotropic peptide and reducing desensitization.

Also, the insulinotropic peptide derivative with a modified N-terminal charge in accordance with the present invention exhibits increased insulinotropic activity and in-vivo blood glucose level-lowering activity due to a change of the binding activity with the GLP-1 receptor as compared to a native insulinotropic peptide.

The insulinotropic peptide derivative according to the present invention can have increased insulinotropic activity as compared to a native insulinotropic peptide and exhibit excellent in-vivo glucose level-lowering activity because the N-terminal charge of the insulinotropic peptide is changed to a neutral or net positive charge to cause a change in the binding activity with the GLP-1 receptor.

In embodiment of the present invention, the insulinotropic peptide derivative, in which the positive charge on the N-terminal amino acid of the insulinotropic peptide is modified to a neutral or net negative charge, has a higher dissociation constant (Kd) from the GLP-1 receptor than that of the native insulinotropic peptide. Accordingly, it has been confirmed that frequent binding and dissociation with the GPL-1 receptor can be repeated (see Example 1). Moreover, it has been confirmed that the insulinotropic peptide derivative, in which the N-terminal charge of the insulinotropic peptide is modified, exhibited an about two-fold increase in insulinotropic activity compared to the native insulinotropic peptide, in which the N-terminal charge of the insulinotropic peptide is not modified (see Example 2). In addition, the insulinotropic peptide derivative, in which the N-terminal charge the insulinotropic peptide is modified, exhibited a five-fold increase in glucose level-lowering activity in diabetic animal models (db/db mice) compared to the native insulinotropic peptide (see Example 3).

Accordingly, can be seen that the insulinotropic peptide derivative, in which the positive charge on the N-terminal amino acid of the insulinotropic peptide is modified according to the present invention, has an increased dissociation constant from GLP-1, i.e., an increase in dissociation from a GLP-receptor, thus showing excellent stability in blood and insulinotropic activity.

As described above, it has been first found by the present application that, if the N-terminal charge of the insulinotropic peptide is modified to a neutral or net negative charge, the binding activity with the GLP-receptor, particularly the dissociation from the above receptor can be increased, thus leading to increased biological activity of the insulinotropic peptide. Accordingly, the excellent stability in blood and insulinotropic activity of the insulinotropic peptide derivative according to the present invention will be useful to maximize the effect of the treatment of type 2 diabetes.

In another embodiment, the present invention provides a pharmaceutical composition for the treatment of diabetes containing as an active ingredient the insulinotropic peptide derivative, in which the N-terminal charge is modified.

The description of the insulinotropic peptide derivative with a modified N-terminal charge is as described above.

The insulinotropic peptide derivative with a modified N-terminal charge according to the present invention has higher insulinotropic activity and glucose level-lowering activity as compared to the native insulinotropic peptide, and thus it can be used as an excellent therapeutic drug for diabetes.

The pharmaceutical compositions for the treatment of diabetes mellitus according to the present invention can be administered to a subject in need thereof to effectively treat diabetes.

Accordingly, a method for treating diabetes in a subject includes administering a therapeutically effective amount of the insulinotropic peptide derivative with modification of the N-terminal charge as previously described, to a subject in need thereof.

The term "treatment" as used herein refers to all of the actions by which the symptoms of diabetes have taken a turn for the better or been modified favorably by administration of the insulinotropic peptide derivative with a modified N-terminal charge or the pharmaceutical composition containing the same.

The term "administration" as used herein refers to introduction of a predetermined amount of the insulinotropic peptide derivative with a modified N-terminal charge or the pharmaceutical composition containing the same into a subject by a certain suitable method. The drug may be administered via any of the common routes, as long as it is able to reach a desired tissue. For example, the modes of administration include intraperitoneal, intravenous, intramuscular, subcutaneous, intradermal, oral, topical, intranasal, intrapulmonary and intrarectal administration, but are not limited thereto. However, since peptides are digested upon oral administration, the composition for oral administration should be coated or formulated for protection against degradation in the stomach. Preferably, the composition may be administered in an injectable form. In addition, the pharmaceutical composition may be administered using a certain apparatus capable of transporting the active ingredients into a target cell.

Further, the pharmaceutical composition including the derivative of the present invention may include a pharmaceutically acceptable carrier. For oral administration, the pharmaceutically acceptable carrier may include a binder, a lubricant, a disintegrant, an excipient, a solubilizer, a dispersing agent, a stabilizer, a suspending agent, a coloring agent, a flavoring agent, etc. For injection preparations, the pharmaceutically acceptable carrier may include a buffering agent, a preserving agent, an analgesic, a solubilizer, an isotonic agent, a stabilizer and the like. For preparations for topical administration, the pharmaceutically acceptable carrier may include a base, an excipient, a lubricant, a preserving agent, etc.

The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups, or wafers. For injection preparations, the pharmaceutical composition may be formulated into an ampule as a single-dose form or a multi-dose container. The pharmaceutical composition may also be formulated into solutions, suspensions, tablets, pills, capsules, and long-acting preparations.

On the other hand, examples of the carrier, the excipient and the diluent suitable for formulations may include lactose, dextrose, sucrose, sorbitol, mannitol, xylitol, erythritol, maltitol, starch, *acacia*, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavors, and antiseptics.

The insulinotropic peptide derivative with modified N-terminal charge according to the present invention and the pharmaceutical composition containing the same is administered in a therapeutically effective amount. In the present invention, the term "therapeutically effective amount" refers to an amount sufficient to treat the disease at a reasonable benefit/risk ratio applicable for medical treatment, and the level of the effective amount may be determined depending on factors including type of patient's disease, sever of illness, drug activity, drug sensitivity, administration time, administration route, dissolution rate, length of treatment, the drug to be used simultaneously, and elements well-known in other medical fields. The insulinotropic peptide derivative with modified N-terminal charge according to the present, invention and the pharmaceutical composition containing the same may be administered as an individual therapeutic agent, or in combination with other therapeutic agent(s), or sequentially or simultaneously with conventional therapeutic agent(s), or it may be subjected to single or multiple administration. In view of all the above elements, it is important to administer an amount that can achieve the maximum effect with the minimum amount without adverse effects, which can be readily determined by one skilled in the art.

The administration frequency and dose of the pharmaceutical composition according to the present invention are determined by the type of diseases to be treated, administration routes, the patient's age, gender, weight, and disease severity as well as by the types of the drug as an active component. Since the pharmaceutical composition of the present invention has excellent durations of in-vivo efficacy and titer, it can significantly reduce the administration frequency and dose of the pharmaceutical drugs.

In the present invention, the "subject" includes humans, monkeys, cows, horses, sheep, pigs, chickens, turkeys, quails, cats, dogs, mice, rats, and guinea pigs, but is not limited thereto. In an embodiment, the subject refers to a mammal, and in another embodiment, the subject refers to a human.

[Mode for Invention]

Hereinafter, the present invention will be described in more detail with reference to Examples. However, these Examples are for illustrative purposes only, and the invention is not intended to be limited to these Examples.

Example 1: Comparison of the Binding Activity of GLP-1 Receptor and the Insulinotropic Peptide Derivative with a Modified N-Terminal Charge The binding activity of the GLP-1 receptor and the insulinotropic peptide derivative with a modified N-terminal charge were measured using a surface plasmon resonance (SPR) apparatus (BIACORE 3000, GE Healthcare). In this case, as the insulinotropic peptide derivative with a modified N-terminal charge, CA-exendin-4, DA-exendin-4, HY-exendin-4, and DA-exendin 4 propyl-amide were used.

CA-exendin-4 is a derivative prepared by removing the alpha-carbon of the N-terminal histidine residue of exendin-4; DA-exendin-4 is a deritivate prepared by removing the N-terminal amino group of exendin-4; HY-exendin-4 is a derivative prepared by substituting the N-terminal amino group of exendin-4 with a hydroxyl group; and DA-exendin-4-propyl-amide is a derivative prepared by removing the N-terminal amino group of exendin-4 while substituting the C-terminal carboxyl group with 3-amino propylamide. In addition, a native exendin-4 (exenatide: BYETTA®) was used as a control. Exendin-4 derivatives with a modified N-terminal charge were synthesized by American Peptide Corporation, and the native exendin-4 was obtained from Amylin Pharmaceuticals.

The GLP-1 receptor was expressed from CHO-DG44 cells in hGLP-1R/GST form. The expressed hGLP-1R/GST was immobilized to a CM5 chip by amine coupling. To the hGLP-1R/GST-immobilized. CM5 chip, the insulinotropic peptide derivatives with a modified N-terminal charge were diluted by concentration and then added to determine the binding activity with the GLP-1 receptor. The binding activity between the insulinotropic peptide derivatives with a modified N-terminal charge and the receptor was analyzed according to a 1:1 Langmuir fitting model and the results are shown in FIGS. 1a to 1e and Table 1 below.

TABLE 1

| Sample | N-terminal charge at pH 7.4 | Ka (1/Ms, ×$10^5$) | kd (1/s, ×$10^4$) | $K_D$ (nM) |
|---|---|---|---|---|
| Native exendin-4 | Positive charge | 3.70 ± 0.06 | 5.26 ± 0.11 | 1.4 ± 0.05 |
| CA-exendin-4 | Neutral charge | 1.20 ± 0.11 | 31.5 ± 0.56 | 26.3 ± 2.08 |
| DA-exendin-4 | | 1.13 ± 0.08 | 36.5 ± 1.40 | 32.2 ± 1.89 |
| DA-exendin-4-propyl-amide | | 1.04 ± 0.11 | 33.5 ± 1.40 | 32.6 ± 4.17 |
| HY-exendin-4 | | 0.90 ± 0.07 | 38.3 ± 1.92 | 42.7 ± 4.10 |

As shown in Table 1 and FIGS. 1a through 1e, it has been confirmed that the N-terminal end of the native exendin-4 has a positive charge, whereas exendin-4 derivatives, where this charge is changed to a neutral charge, exhibited a significantly increased dissociation constant (kd). These results show that that more frequent coupling/dissociation can occur repeatedly between the GLP-1 receptor and the insulinotropic peptide derivative with a modified N-terminal charge.

These pharmacokinetic changes in the GLP-1 receptor can prevent clearance of the insulinotropic peptide derivative by the receptor and make desensitization less likely to occur. Therefore, the insulinotropic peptide derivative with a modified N-terminal charge is advantageous for increasing stability in blood.

Example 2: Measurement of Insulinotropic Activity of the Insulinotropic Peptide Derivative with a Modified N-Terminal Charge The insulinotropic activities of the insulinotropic peptide derivatives with a modified N-terminal charge were compared in RINm5F cells. RINm5F cells were thawed, and subcultured at least once, followed by inoculation into a 96-well plate at a density of 1×$10^5$ cells/well with a culture medium containing FBS (Gibco, #11082). Then, the cells were cultured in a 5% $CO_2$ incubator at 37° C. for 48 hours. For the measurement of the insulinotropic activities, the culture medium of RINm5F cells was replaced with a fresh medium containing 0.5% FBS, and then incubated for 1 hour.

Each of the insulinotropic peptide derivatives with a modified N-terminal charge and a native exendin-4 (exenatide: BYETTA®) was diluted with a culture medium containing 0.5% FBS and glucose to yield concentrations from 10 nM to 0.001 nM. At this time, the culture medium not containing exendin-4 was used as a control group. The culture medium of RINm5F cells was removed, and the prepared samples were added thereto, followed by culturing in a 5% $CO_2$ incubator at 37° C. for 1 hour. Then, the medium was recovered from each well. A rat insulin ELISA kit (Mercodia) was used to determine the insulin concentrations of the recovered medium, and the results are shown in FIG. 2 and Table 2.

TABLE 2

| Sample | Ratio of maximum insulin secretion to control group |
|---|---|
| Insulinotropic peptide derivatives with a modified N-terminal charge | 198.9% |
| Native exendin-4 | 159.0% |

Figure 2:
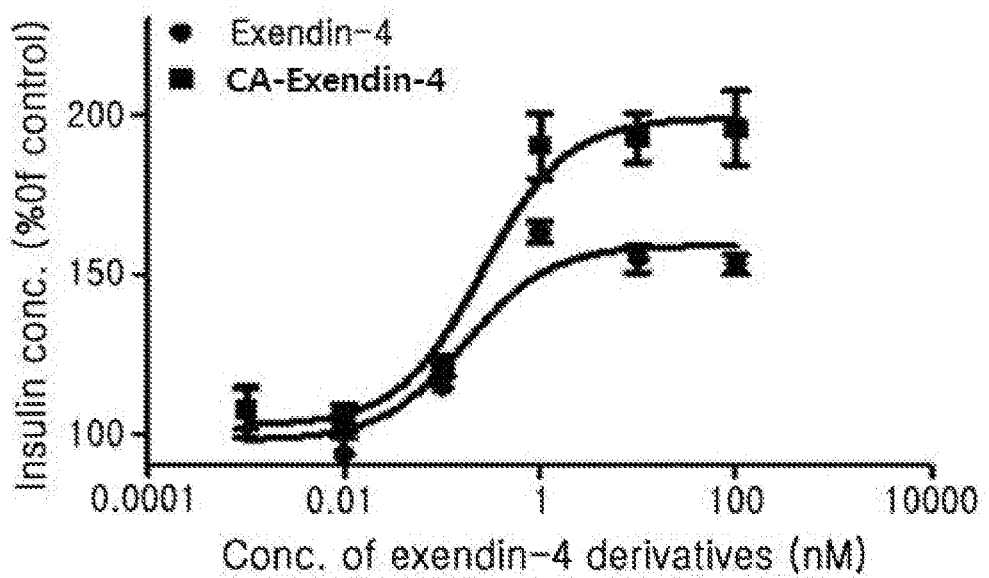
FIG. 2 shows a result of measurement of insulinotropic activity of native exendin-4 and a CA-exendin-4 derivative with a modified N-terminal charge according to the present invention.

As shown in Table 2 and FIG. 2, it was found that the insulinotropic peptide derivatives with a modified N-terminal charge according to the present invention exhibited about 1.25-fold higher insulinotropic activity than native exendin-4 at the same concentration range.

Example 3: Comparison of In-Vivo Efficacy of the Insulinotropic Peptide Derivative with a Modified N-Terminal Charge To measure in-vivo efficacy of the insulinotropic peptide derivatives with a modified N-terminal charge, their blood glucose lowering effect was measured in a diabetic animal model, as compared with native exendin-4. The db/db mice (Jackson Lab, 10-12 week-old) were made to fast for 2 hours, and then the insulinotropic peptide derivatives with a modified N-terminal charge and exendin-4 (exenatide: BYETTA®) were administered at an amount of 0.01-1000 mcg/kg via a subcutaneous route, respectively. At this time, a vehicle was similarly administered as a control group, and % change of blood glucose vs. the vehicle was calculated at each concentration. After 1 hour, blood samples were collected from a tail blood vessel to measure blood glucose levels using a glucometer. At each concentration, the $ED_{50}$ for the blood glucose level-lowering effect vs. the vehicle was calculated using the Prism program.

TABLE 3

| Sample | $ED_{50}$ (mcg/kg) | $R^2$ |
|---|---|---|
| Insulinotropic peptide derivatives with a modified N-terminal charge | 2.30 | 0.99 |
| Native exendin-4 | 9.92 | 0.98 |

Figure 3:
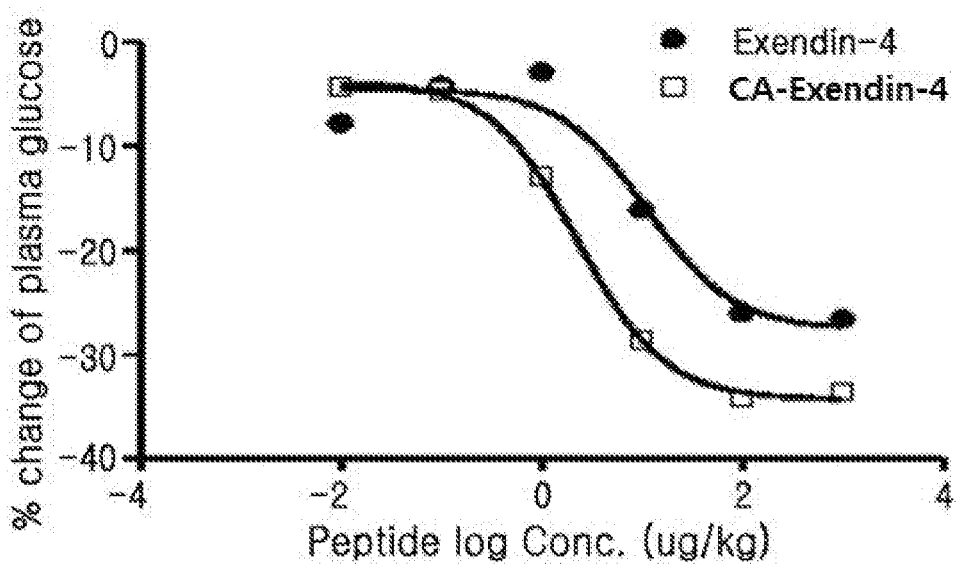
FIG. 3 shows a result of measurement of blood glucose level-lowering activity of native exendin-4 and a CA-exendin-4 derivative with a modified N-terminal charge according to the present invention in diabetic animal models.

As shown in Table 3 and FIG. 3, it was found that the insulinotropic peptide derivatives with a modified N-terminal charge according to the present invention exhibited an about 5-fold higher blood glucose level-lowering effect than native exendin-4 in the diabetic animal model.

From the above-described results, it can be seen that the insulinotropic peptide derivative with a modified N-terminal charge according to the present invention can be rapidly dissociated from the GLP-1 receptor due to an increase in the dissociation constant with the GLP-1 and thus exhibits stability in blood, causing increased insulinotropic activity and a blood glucose level-lowering effect. Therefore, the insulinotropic peptide derivative according to the present invention can be very effectively used for the treatment of diabetes.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects and that all changes and modifications that are derived from the subject matter defined in the claims or equivalents thereof are intended to be embraced in the scope of the present invention.

INDUSTRIAL APPLICABILITY

The insulinotropic peptide derivative with a modified N-terminal charge according to the present invention can be rapidly dissociated from the GLP-1 receptor and thus it can prevent clearance of the insulinotropic peptide and is less likely to cause desensitization. Also, the insulinotropic peptide derivative with a modified N-terminal charge in accordance with the present invention exhibits increased insulinotropic activity and an in-vivo blood glucose level-lowering effect due to a change of the binding activity with the GLP-1 receptor as compared to a native insulinotropic peptide. Therefore, the insulinotropic peptide derivative according to the present invention can be very effectively used for the treatment of diabetes.

The invention claimed is:

1. An insulinotropic peptide derivative,
wherein a positive charge on the N-terminal amino group or N-terminal amino acid residue of a native insulinotropic peptide or its analogue or a fragment thereof is chemically modified to a neutral or net negative charge; and
wherein the C-terminal carboxyl group of the native insulinotropic peptide or its analogue or a fragment thereof is substituted with 3-amino propylamide.

2. The insulinotropic peptide derivative of claim 1, wherein the N-terminal residue of the native insulinotropic peptide, or its analogue, or a fragment thereof is histidine, and the modification is removal or substitution of the alpha-amino group of the histidine residue, or removal of the alpha-carbon, thereby having a neutral or net negative charge.

3. The insulinotropic peptide derivative of claim 2, wherein the modification is at least one selected from the group consisting of:
removing the N-terminal amino group of the native insulinotropic peptide, or its analogue or a fragment thereof;
substituting the N-terminal amino group of the native insulinotropic peptide, or its analogue or a fragment thereof with a hydroxyl group;
modifying the N-terminal amino group of the native insulinotropic peptide, or its analogue or a fragment thereof with two methyl groups;
substituting the N-terminal amino group of the native insulinotropic peptide, or its analogue or a fragment thereof with a carboxyl group; and
removing the alpha-carbon of the N-terminal histidine residue of the native insulinotropic peptide, or its analogue or a fragment thereof thereby leaving only the imidazoacetyl group.

4. The insulinotropic peptide derivative of claim 3, wherein the N-terminal residue of the native insulinotropic peptide or its analogue or a fragment thereof is substituted with a group selected from desamino-histidyl, dimethyl-histidyl, beta-hydroxy imidazopropionyl, 4-imidazoacetyl, or beta-carboxyimidazopropionyl.

5. The insulinotropic peptide derivative of claim 4, wherein the N-terminal residue of the native insulinotropic peptide or its analogue or a fragment thereof is substituted with desamino-histidyl.

6. The insulinotropic peptide derivative of claim 1, wherein the insulinotropic peptide derivative has a binding activity with a glucagon-like peptide-1 (GLP-1) receptor.

7. The insulinotropic peptide derivative of claim 1, wherein the native insulinotropic peptide or its analogue or a fragment thereof is glucagon-like peptide-1 (GLP-1) of SEQ ID NO: 1, exendin-4 of SEQ ID NO: 2, exendin-3 of SEQ ID NO: 3, oxyntomodulin of SEQ ID NO: 5, glucose-dependent insulinotropic polypeptide (GIP) of SEQ ID NO: 6, an analogue thereof, or a fragment thereof.

8. The insulinotropic peptide derivative of claim 7, wherein the native insulinotropic peptide or its analogue or a fragment thereof is a GLP-1 analogue, and is selected from the group consisting of $Arg^{34}$-GLP-1(7-37), $Gly^8$-GLP-1(7-36)-amide, $Gly^8$-GLP-1(7-37), $Val^8$-GLP-1(7-36)-amide, $Val^8$-GLP-1(7-37), $Val^8Asp^{22}$-GLP-1(7-36)-amide, $Val^8Asp^{22}$-GLP-1(7-37), $Val^8Glu^{22}$-GLP-1(7-36)-amide, $Val^8Glu^{22}$-GLP-1(7-37), $Val^8Lys^{22}$-GLP-1(7-36)-amide, $Val^8Lys^{22}$-GLP-1(7-37), $Val^8Arg^{22}$-GLP-1(7-36)-amide, $Val^8Arg^{22}$-GLP-1(7-37), $Val^8His^{22}$-GLP-1(7-36)-amide, $Val^8His^{22}$-GLP-1(7-37), $Val^8Trp^{16}Glu^{22}$-GLP-1(7-37), $Val^8Glu^{22}Val^{25}$-GLP-1(7-37), $Val^8Tyr^{16}Glu^{22}$-GLP-1(7-37), $Val^8Trp^{16}Glu^{22}$-GLP-1(7-37), $Val^8Leu^{16}Glu^{22}$-GLP-1(7-37), $Val^8Tyr^{18}Glu^{22}$-GLP-1(7-37), $Val^8Glu^{22}His^{37}$-GLP-1(7-37), $Val^8Glu^{22}Ile^{33}$-GLP-1(7-37), $Val^8Trp^{16}Glu^{22}Val^{25}Ile^{33}$-GLP-1(7-37), $Val^8Trp^{16}Glu^{22}Ile^{33}$-GLP-1(7-37), $Val^8Glu^{22}Val^{25}Ile^{33}$-GLP-1(7-37), and $Val^8Trp^{16}Glu^{22}Val^{25}$-GLP-1(7-37).

9. The insulinotropic peptide derivative of claim 7, wherein the native insulinotropic peptide derivative or its analogue or a fragment thereof is a ZP-10 ($Ser^{38}Lys^{39}$-exendin-4(1-39)-LysLysLysLysLys-amide), which is an exendin-4 analogue represented by SEQ ID NO: 4.

10. The insulinotropic peptide derivative of claim 5, wherein the native insulinotropic peptide or an analogue thereof is GLP-1, exendin-4, exendin-3, oxyntomodulin, GIP or an analogue thereof, and wherein the N-terminal histidine residue of GLP-1, exendin-4, exendin-3, oxyntomodulin, GIP or an analogue thereof is substituted with desamino-histidyl, and the C-terminal carboxyl group of GLP-1, exendin-4, exendin-3, oxyntomodulin, GIP or an analogue thereof is substituted with 3-amino propylamide.

11. The insulinotropic peptide derivative of claim 10, wherein the insulinotropic peptide derivative is desamino-histidyl (DA)-exendin-4-propyl-amide prepared by removing the N-terminal amino group of exendin-4 and substituting the C-terminal carboxyl group with 3-amino propylamide.

12. A pharmaceutical composition for the treatment of diabetes comprising the insulinotropic peptide derivative of claim 1 as an active ingredient.

13. A method for treating diabetes comprising administering a therapeutically effective amount of the insulinotropic peptide derivative as defined in claim 1 to a subject in need thereof.

* * * * *

SEQUENCE LISTING

```
<160> NUMBER OF SEQ ID NOS: 10

<210> SEQ ID NO 1
<211> LENGTH: 31
<212> TYPE: PRT
<213> ORGANISM: Homo sapiens

<400> SEQUENCE: 1

His Ala Glu Gly Thr Phe Thr Ser Asp Val Ser Ser Tyr Leu Glu Gly
 1               5                  10                  15

Gln Ala Ala Lys Glu Phe Ile Ala Trp Leu Val Lys Gly Arg Gly
            20                  25                  30

<210> SEQ ID NO 2
<211> LENGTH: 39
<212> TYPE: PRT
<213> ORGANISM: Heloderma suspecturm

<400> SEQUENCE: 2

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma horridum

<400> SEQUENCE: 3

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 44
```

```
<212> TYPE: PRT
<213> ORGANISM: Artificial Sequence
<220> FEATURE:
<223> OTHER INFORMATION: Synthetic construct of ZP-10
<220> FEATURE:
<221> NAME/KEY: MOD_RES
<222> LOCATION: (44)
<223> OTHER INFORMATION: Amidation of carboxyl group

<400> SEQUENCE: 4

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 5
<211> LENGTH: 37
<212> TYPE: PRT
<213> ORGANISM: Homo sapiens

<400> SEQUENCE: 5

His Ser Gln Gly Thr Phe Thr Ser Asp Tyr Ser Lys Tyr Leu Asp Ser
 1               5                  10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 6
<211> LENGTH: 42
<212> TYPE: PRT
<213> ORGANISM: Homo sapiens

<400> SEQUENCE: 6

Tyr Ala Glu Gly Thr Phe Ile Ser Asp Tyr Ser Ile Ala Met Asp Lys
 1               5                  10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 7
<211> LENGTH: 30
<212> TYPE: PRT
<213> ORGANISM: Artificial Sequence
<220> FEATURE:
<223> OTHER INFORMATION: Synthetic construct

<400> SEQUENCE: 7

Ala Glu Gly Thr Phe Thr Ser Asp Val Ser Ser Tyr Leu Glu Gly Gln
 1               5                  10                  15

Ala Ala Lys Glu Phe Ile Ala Trp Leu Val Lys Gly Arg Gly
            20                  25                  30

<210> SEQ ID NO 8
<211> LENGTH: 38
<212> TYPE: PRT
<213> ORGANISM: Artificial Sequence
<220> FEATURE:
<223> OTHER INFORMATION: Synthetic construct

<400> SEQUENCE: 8
```

```
Ser Asp Gly Thr Phe Thr Ser Asp Leu Ser Lys Gln Met Glu Glu Glu
 1               5                   10                  15

Ala Val Arg Leu Phe Ile Glu Trp Leu Lys Asn Gly Gly Pro Ser Ser
            20                  25                  30

Gly Ala Pro Pro Pro Ser
            35

<210> SEQ ID NO 9
<211> LENGTH: 38
<212> TYPE: PRT
<213> ORGANISM: Artificial Sequence
<220> FEATURE:
<223> OTHER INFORMATION: Synthetic construct

<400> SEQUENCE: 9

Gly Glu Gly Thr Phe Thr Ser Asp Leu Ser Lys Gln Met Glu Glu Glu
 1               5                   10                  15

Ala Val Arg Leu Phe Ile Glu Trp Leu Lys Asn Gly Gly Pro Ser Ser
            20                  25                  30

Gly Ala Pro Pro Pro Ser
            35

<210> SEQ ID NO 10
<211> LENGTH: 36
<212> TYPE: PRT
<213> ORGANISM: Artificial Sequence
<220> FEATURE:
<223> OTHER INFORMATION: Synthetic construct

<400> SEQUENCE: 10

Ser Gln Gly Thr Phe Thr Ser Asp Tyr Ser Lys Tyr Leu Asp Ser Arg
 1               5                   10                  15

Arg Ala Gln Asp Phe Val Gln Trp Leu Met Asn Thr Lys Arg Asn Arg
            20                  25                  30

Asn Asn Ile Ala
        35
```